(12) United States Patent
Zaiki

(10) Patent No.: US 8,876,378 B2
(45) Date of Patent: Nov. 4, 2014

(54) X-RAY DIAGNOSTIC APPARATUS

(71) Applicant: Ryuji Zaiki, Utsunomiya (JP)

(72) Inventor: Ryuji Zaiki, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 145 days.

(21) Appl. No.: 13/724,481

(22) Filed: Dec. 21, 2012

(65) Prior Publication Data

US 2013/0114797 A1    May 9, 2013

Related U.S. Application Data

(63) Continuation of application No. PCT/JP2012/063152, filed on May 23, 2012.

(30) Foreign Application Priority Data

May 23, 2011    (JP) .................................. 2011-115238

(51) Int. Cl.
| | | |
|---|---|---|
| A61B 6/08 | (2006.01) | |
| A61B 6/00 | (2006.01) | |
| A61B 6/10 | (2006.01) | |
| A61B 6/04 | (2006.01) | |

(52) U.S. Cl.
CPC .................. *A61B 6/04* (2013.01); *A61B 6/0407* (2013.01); *A61B 6/547* (2013.01); *A61B 6/107* (2013.01); *A61B 6/503* (2013.01); *A61B 6/504* (2013.01); *A61B 6/4441* (2013.01)
USPC ........................................... 378/197; 378/195

(58) Field of Classification Search
USPC .................... 378/195, 196, 197, 198
See application file for complete search history.

(56) References Cited

U.S. PATENT DOCUMENTS

| 4,481,657 A | 11/1984 | Larsson | |
|---|---|---|---|
| 6,120,180 A * | 9/2000 | Graumann | .................... 378/206 |
| 6,609,826 B1 * | 8/2003 | Fujii et al. | ..................... 378/198 |

(Continued)

FOREIGN PATENT DOCUMENTS

| JP | 63-234948 A | 9/1988 |
|---|---|---|
| JP | 2-57931 B2 | 12/1990 |

(Continued)

OTHER PUBLICATIONS

International Preliminary Report on Patentability and Written Opinion issued Nov. 26, 2013 in PCT/JP2012/063152 (submitting English translation only).

(Continued)

*Primary Examiner* — Hoon Song
(74) *Attorney, Agent, or Firm* — Oblon, Spivak, McClelland, Maier & Neustadt, L.L.P.

(57) ABSTRACT

According to one embodiment, an X-ray diagnostic apparatus includes at least a tabletop support, an arm, a position storing unit, and a mechanism controlling unit. The tabletop support supports a tabletop movably in a longitudinal direction, a raising/reclining direction, and an upper/lower direction of the tabletop. The arm holds an X-ray tube and an X-ray detector movably in an approaching/separating direction with respect to the tabletop support. The position storing unit stores a photographing position of the arm and a photographing position of the tabletop in association with each other. When the arm is at a retraction position, the mechanism controlling unit moves the tabletop in the raising/reclining direction and the upper/lower direction to maintain a position in at least the upper/lower direction of a region of the object corresponding to a photographing position of the arm stored by the position storing unit.

5 Claims, 6 Drawing Sheets

(56) References Cited

U.S. PATENT DOCUMENTS

| | | | |
|---|---|---|---|
| 8,242,925 B2 * | 8/2012 | Graumann et al. | 340/686.2 |
| 2004/0098804 A1 | 5/2004 | Varadharajulu et al. | |
| 2004/0172757 A1 | 9/2004 | Somasundaram | |
| 2005/0114996 A1 | 6/2005 | Somasundaram | |

FOREIGN PATENT DOCUMENTS

| | | |
|---|---|---|
| JP | 11-206744 A | 8/1999 |
| JP | 2000-005161 A | 1/2000 |
| JP | 2003-210447 A | 7/2003 |
| JP | 2004-174250 A | 6/2004 |
| JP | 4269307 B2 | 3/2009 |

OTHER PUBLICATIONS

International Search Report for International Application No. PCT/JP2012/063152 dated Jul. 31, 2012 (with English translation).

* cited by examiner

X-RAY DIAGNOSTIC APPARATUS

CROSS-REFERENCE TO RELATED APPLICATIONS

This application is a Continuation Application of No. PCT/JP2012/063152, filed on May 23, 2012, and the PCT application is based upon and claims the benefit of priority from Japanese Patent Application No. 2011-115238, filed on May 23, 2011, the entire contents of which are incorporated herein by reference.

FIELD

Embodiments described herein relate generally to an X-ray diagnostic apparatus.

BACKGROUND

In recent years, along with developments in angiography and interventional radiology (IVR) using catheters, X-ray diagnostic apparatuses have made progress mainly in the field of circulatory organs. The X-ray diagnostic apparatuses for circulatory organs have an expanding application range as an advanced IVR system, and thus are applied to, for example, stent-graft treatment combined with a surgical operation.

Such an X-ray diagnostic apparatus for circulatory organs includes: a radiography unit including an X-ray irradiating portion, an X-ray detecting portion, and an arm that holds the X-ray irradiating portion and the X-ray detecting portion in the vicinity of both ends of the arm; and a bed portion that supports a tabletop on which an object is placed, movably in a longitudinal direction, an upper/lower direction, and a raising/reclining direction of the tabletop. Then, the arm and the tabletop are moved such that an interest part of the object does not come out of a field of irradiation, which enables photographing at various angles.

The radiography unit and the bed portion are installed in an examination room with equipment capable of surgical treatment and the like. When the radiography unit is not used, the radiography unit may be brought away and retracted from the bed portion so as not to obstruct the surgical treatment, and the tabletop may then be moved in the raising/reclining direction for the purpose of facilitating the surgical treatment.

Unfortunately, if the tabletop is moved in the raising/reclining direction after the retraction of the radiography unit, the interest part comes out of a height for photographing, and hence a height of the tabletop needs to be adjusted, resulting in a trouble for an operator who performs an operation such as surgical treatment.

The present embodiment has been made in order to solve the above-mentioned problem, and therefore has an object to provide an X-ray diagnostic apparatus that can reduce an amount of work.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of an X-ray diagnostic apparatus according to embodiments of the present invention with reference to the drawings.

In general, according to one embodiment, an X-ray diagnostic apparatus includes a tabletop on which an object is placed, a tabletop support, an arm, a position storing unit, and a mechanism controlling unit. The tabletop support supports the tabletop movably in a longitudinal direction, a raising/reclining direction, and an upper/lower direction of the tabletop. The arm holds an X-ray tube and an X-ray detector movably in an approaching/separating direction with respect to the tabletop support. Here, the X-ray tube irradiates the object placed on the tabletop with X-rays, and the X-ray detector detects X-rays transmitted through the object. The position storing unit stores a photographing position of the arm and a photographing position of the tabletop in association with each other for each photographing of the object. When the arm is at a retraction position at which irradiation of the object on the tabletop with X-rays is impossible, the mechanism controlling unit moves the tabletop in the raising/reclining direction and the upper/lower direction so as to maintain a position in at least the upper/lower direction of a region of the object corresponding to a photographing position of the arm stored by the position storing unit.

Figure 1:
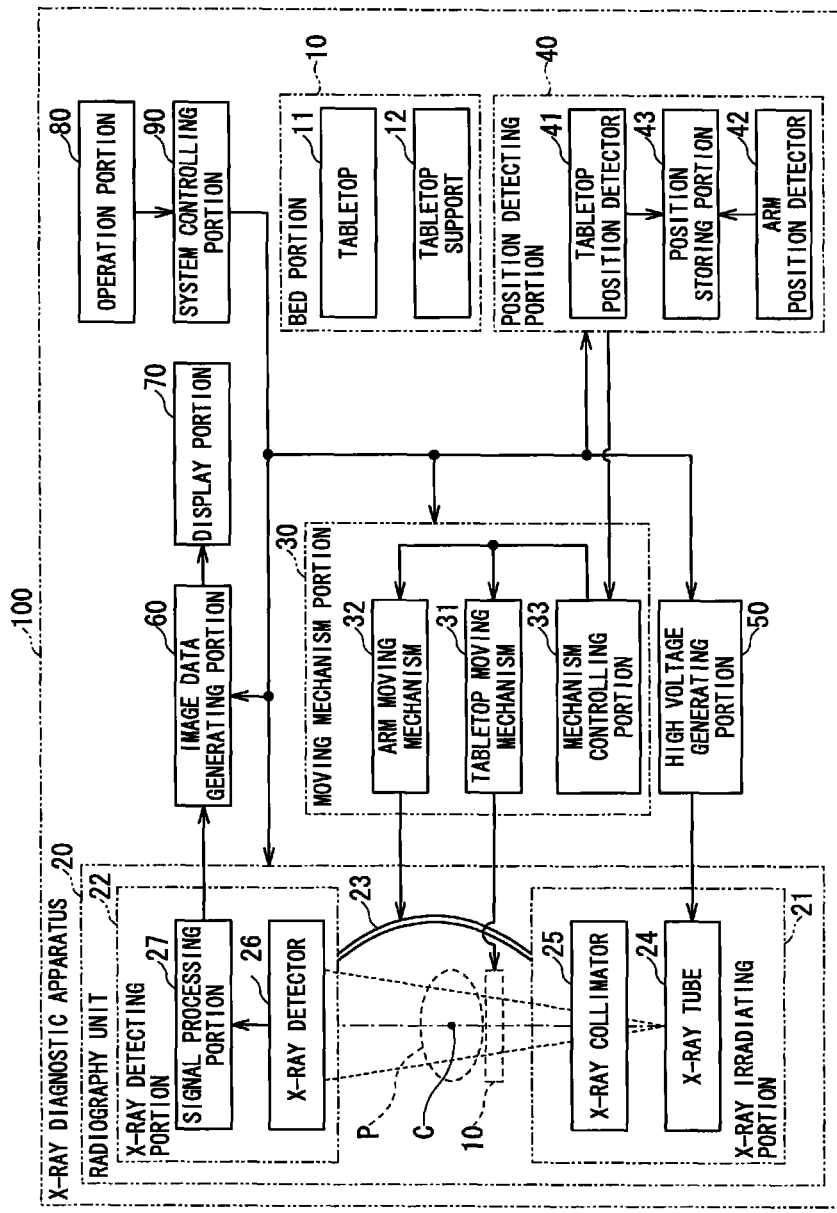
FIG. 1 is a block diagram illustrating a configuration of an X-ray diagnostic apparatus according to an embodiment.

FIG. 1 is a block diagram illustrating a configuration of an X-ray diagnostic apparatus. An X-ray diagnostic apparatus 100 includes: a bed portion 10 on which an object P is movably placed; a radiography unit 20 that irradiates, with X-rays, the object P placed on the bed portion 10 to photograph the object P; a moving mechanism portion 30 that moves respective units of the bed portion 10 and the radiography unit 20; a position detecting portion 40 that detects positions of the units moved by the moving mechanism portion 30; and a high voltage generating portion 50 that generates a high voltage necessary for X-ray irradiation by the radiography unit 20.

The X-ray diagnostic apparatus 100 also includes: an image data generating portion 60 that generates image data from X-ray projection data generated in photographing by the radiography unit 20; a display portion 70 that displays the image data generated by the image data generating portion 60; an operation portion 80 that serves to make inputs for setting examination information containing X-ray irradiation conditions, a photographed region of the object P irradiated with X-rays, and the like as well as inputs of various commands; and a system controlling portion 90 that comprehensively controls the radiography unit 20, the moving mechanism portion 30, the position detecting portion 40, the high voltage generating portion 50, and the image data generating portion 60.

The bed portion 10 includes: a tabletop 11 on which the object P is placed; and a tabletop support 12 that supports the tabletop 11 movably in a longitudinal direction, a raising/reclining direction, and an upper/lower direction of the tabletop 11.

The radiography unit 20 includes: an X-ray irradiating portion 21 that irradiates, with X-rays, the object P placed on the tabletop 11 of the bed portion 10; an X-ray detecting portion 22 that detects X-rays that are transmitted through the object P as a result of the X-ray irradiation by the X-ray irradiating portion 21, to generate the X-ray projection data; and an arm 23 that holds the X-ray irradiating portion 21 and the X-ray detecting portion 22 movably in an approaching/separating direction with respect to the bed portion 10.

The X-ray irradiating portion 21 includes: an X-ray tube 24 that generates X-rays; and an X-ray collimator 25 that restricts an irradiation range of the object P with the X-rays emitted from the X-ray tube 24, and is disposed between the X-ray tube 24 and the object P. The X-ray detecting portion 22 includes: an X-ray detector 26 that is disposed so as to be opposed to the X-ray irradiating portion 21, and detects the X-rays transmitted through the object P to convert the X-rays into an electrical signal; and a signal processing portion 27 that processes the electrical signal converted by the X-ray detector 26 to generate the X-ray projection data.

The arm 23 holds the X-ray irradiating portion 21 and the X-ray detecting portion 22 movably in the direction approaching the bed portion 10 and the direction separating from the bed portion 10 and in a rotatable manner.

The moving mechanism portion 30 includes: a tabletop moving mechanism 31 that moves the tabletop 11 in the bed portion 10 in the longitudinal direction, the raising/reclining direction, and the upper/lower direction; an arm moving mechanism 32 that moves and rotates the arm 23 in the radiography unit 20 in the approaching/separating direction; and a mechanism controlling portion 33 that controls the tabletop moving mechanism 31 and the arm moving mechanism 32 on the basis of positions of the tabletop 11 and the arm 23 detected by the position detecting portion 40.

The position detecting portion 40 includes: a tabletop position detector 41 that detects positions in the longitudinal direction, the raising/reclining direction, and the upper/lower direction of the tabletop 11 of the bed portion 10; an arm position detector 42 that detects positions in the approaching/separating direction and the rotating direction of the arm 23 of the radiography unit 20; and a position storing portion 43 that stores the positions of the tabletop 11 detected by the tabletop position detector 41 and the positions of the arm 23 detected by the arm position detector 42.

The high voltage generating portion 50 includes: a high voltage generator that supplies a high voltage to the X-ray tube 24 of the X-ray irradiating portion 21 in the radiography unit 20; and an X-ray controlling portion that controls the high voltage generator. The high voltage generating portion 50 supplies, to the X-ray tube 24, a high voltage for generating X-rays for fluoroscopy or X-rays for photographing with higher energy than that of the X-rays for fluoroscopy, on the basis of X-ray irradiation conditions that are supplied by the system controlling portion 90 and include a tube voltage and a tube current.

The image data generating portion 60 generates image data from the X-ray projection data that is outputted on a line basis by the signal processing portion 27 of the X-ray detecting portion 22 in the radiography unit 20, and outputs the generated image data to the display portion 70.

The display portion 70 includes a liquid crystal panel monitor or a CRT monitor, and displays the image data generated by the image data generating portion 60.

The operation portion 80 is an interactive interface including input devices such as a keyboard, a trackball, a joystick, and a mouse, a display panel, and various switches, and serves to make inputs for setting photographing conditions. The operation portion 80 also serves to make inputs for setting examination information such as: examination regions of a head, a chest, and an abdomen of the object P to be examined or surgically treated; and an age and a height of the object P. The operation portion 80 also serves to make inputs for moving the tabletop 11 of the bed portion 10 and the arm 23 of the radiography unit 20.

The system controlling portion 90 includes a CPU and a storage circuit. The system controlling portion 90 once stores input information such as examination information inputted through the operation portion 80, and then controls the radiography unit 20, the moving mechanism portion 30, the position detecting portion 40, the high voltage generating portion 50, and the image data generating portion 60 on the basis of the stored input information.

Figure 2:
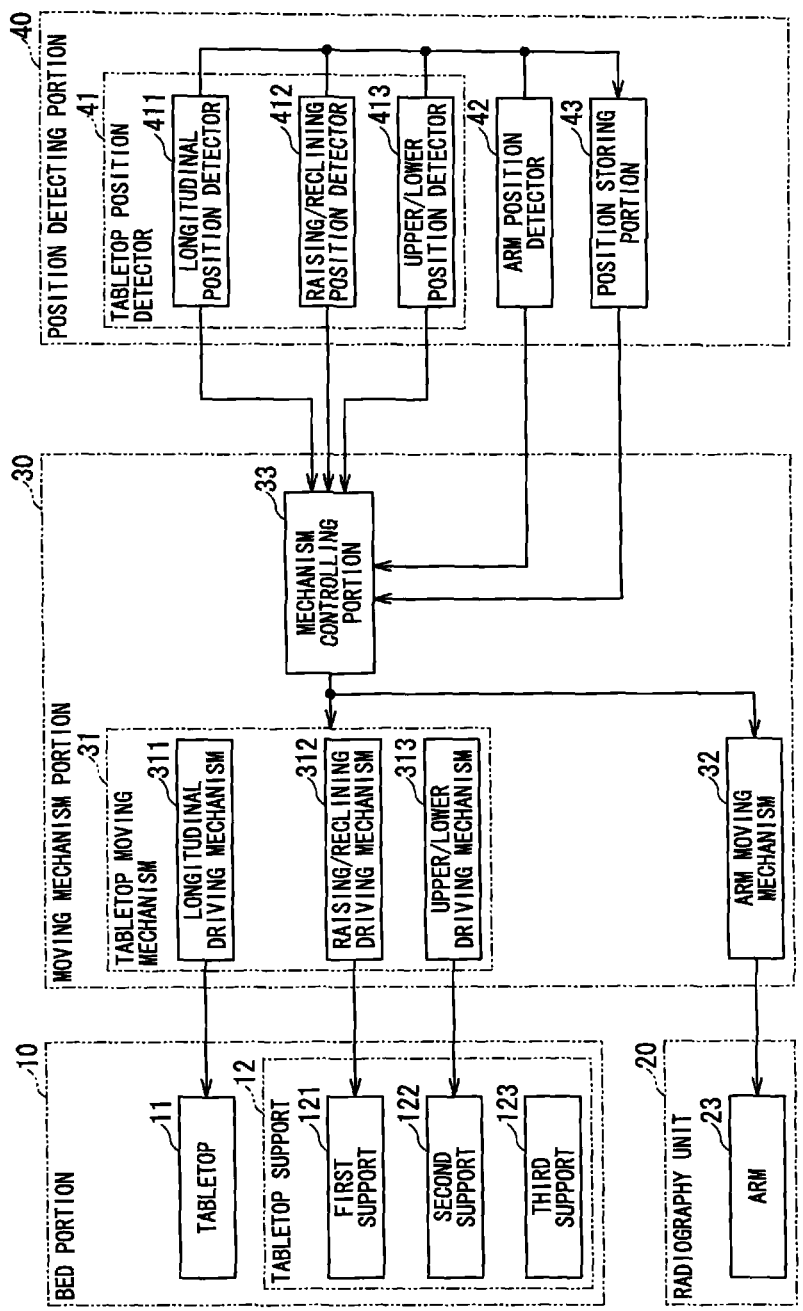
FIG. 2 is a block diagram illustrating detailed configurations of a bed portion, a moving mechanism portion, and a position detecting portion according to the embodiment.
Figure 3:
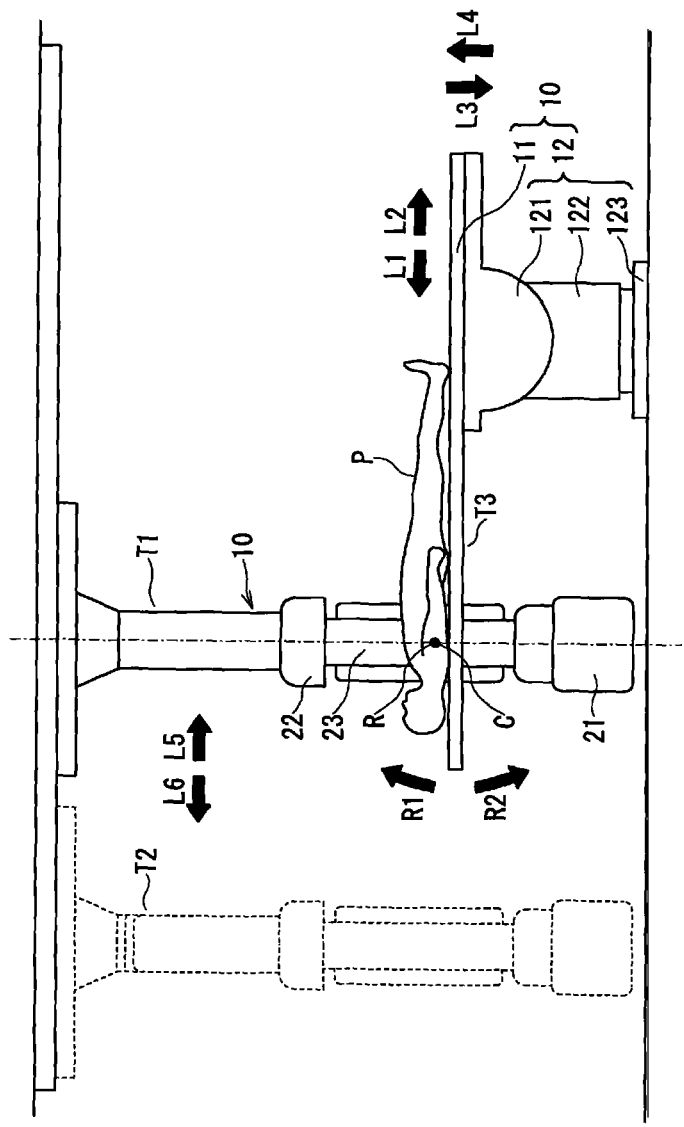
FIG. 3 is a view illustrating placements and moving directions of the bed portion and a radiography unit according to the embodiment.

Next, with reference to FIG. 1 to FIG. 3, description is given in detail of configurations of the bed portion 10, the moving mechanism portion 30, and the position detecting portion 40 and moving directions of the bed portion 10 and the radiography unit 20 moved by the moving mechanism portion 30.

FIG. 2 is a block diagram illustrating detailed configurations of the bed portion 10, the moving mechanism portion 30, and the position detecting portion 40. The tabletop support 12 of the bed portion 10 includes: a first support 121 that supports the tabletop 11 movably in the longitudinal direction; a second support 122 that rotatably supports the first support 121; and a third support 123 that supports the second support 122 movably in the upper/lower direction.

The tabletop moving mechanism 31 of the moving mechanism portion 30 is disposed in the bed portion 10, and includes: a longitudinal driving mechanism 311 that moves the tabletop 11 of the bed portion 10 in the longitudinal direction; a raising/reclining driving mechanism 312 that moves the tabletop 11 in the raising/reclining direction; and an upper/lower driving mechanism 313 that moves the tabletop 11 in the upper/lower direction.

FIG. 3 is a view illustrating placements and moving directions of the bed portion 10 and the radiography unit 20.

The longitudinal driving mechanism 311 of the tabletop moving mechanism 31 in the moving mechanism portion 30 is disposed in the first support 121 of the tabletop support 12 in the bed portion 10, and moves the tabletop 11 in an arrow L1 direction and an arrow L2 direction opposite to the L1 direction, the arrow L1 and L2 directions corresponding to the longitudinal direction.

The raising/reclining driving mechanism 312 is disposed in the second support 122 of the tabletop support 12, and rotationally drives the first support 121. The raising/reclining driving mechanism 312 moves the tabletop 11 by this rotational driving in an arrow R1 direction and an arrow R2 direction opposite to the R1 direction, the arrow R1 and R2 directions corresponding to the raising/reclining direction, in which the tabletop 11 is rotated along a tilt axis parallel to a lateral direction of the tabletop 11.

The upper/lower driving mechanism 313 is disposed in the third support 123 of the tabletop support 12, and drives the second support 122 upward/downward to thereby move the tabletop 11 in an arrow L3 direction corresponding to the lower direction and an arrow L4 direction corresponding to the upper direction.

The arm moving mechanism 32 moves the arm 23 of the radiography unit 20 in an arrow L5 direction and an arrow L6 direction opposite to the arrow L5 direction, the arrow L5 and L6 directions corresponding to the approaching/separating direction. Then, the arm moving mechanism 32 moves the arm 23 in the L5 direction corresponding to the direction approaching the bed portion 10, and stops the arm 23 at a photographing position T1 at which an interest part R as the examination region of the object P on the tabletop 11 can be irradiated with X-rays. Conversely, when irradiation with X-rays is stopped, the arm moving mechanism 32 moves the arm 23 in the L6 direction corresponding to the direction separating from the bed portion 10, and stops the arm 23 at a retraction position T2 at which the radiography unit 20 is brought away from the tabletop 11 and the interest part R of the object P on the tabletop 11 cannot be irradiated with X-rays.

In addition, at the time of photographing by the radiography unit 20, the arm moving mechanism 32 rotationally moves the arm 23 about an isocenter C that is an intersection point between: an illumination axis connecting a focal point of the X-ray tube 24 of the X-ray irradiating portion 21 and a detection surface center of the X-ray detector 26 of the X-ray detecting portion 22; and a straight line passing through a tilt axis of the arm 23.

The tabletop position detector 41 of the position detecting portion 40 illustrated in FIG. 2 is disposed in the tabletop moving mechanism 31 of the moving mechanism portion 30, and includes: a longitudinal position detector 411 that detects a position in the longitudinal direction of the tabletop 11 of the bed portion 10; a raising/reclining position detector 412 that detects a position in the raising/reclining direction of the tabletop 11; and an upper/lower position detector 413 that detects a position in the upper/lower direction of the tabletop 11.

The longitudinal position detector 411 is disposed in the longitudinal driving mechanism 311 of the tabletop moving mechanism 31, and detects a position (longitudinal moving position) of the tabletop 11 moving in the longitudinal direction with respect to the first support 121 of the tabletop support 12 in the bed portion 10. Then, the longitudinal position detector 411 outputs the detected longitudinal moving position to the mechanism controlling portion 33 of the moving mechanism portion 30.

As illustrated in FIG. 3, the longitudinal position detector 411 also detects a position in the longitudinal direction at a photographing position T3 (longitudinal photographing position) of the tabletop 11. At the photographing position T3, the interest part R of the object P can be irradiated with X-rays as a result of: aligning the interest part R onto the isocenter C of the arm 23 at the photographing position T1 of the radiography unit 20; and thus positioning the object P with respect to the arm 23. Then, the longitudinal position detector 411 outputs the detected longitudinal photographing position to the position storing portion 43.

The raising/reclining position detector 412 is disposed in the raising/reclining driving mechanism 312 of the tabletop moving mechanism 31, and detects an angle of the first support 121 being driven with respect to the second support 122, to thereby detect a position (raising/reclining moving position) of the tabletop 11 moving in the raising/reclining direction. Then, the raising/reclining position detector 412 outputs the detected raising/reclining moving position to the mechanism controlling portion 33.

The raising/reclining position detector 412 also detects a position in the raising/reclining direction at the photographing position T3 (raising/reclining photographing position) of the tabletop 11 when the object P is positioned with respect to the arm 23 at the photographing position T1, and outputs the detected raising/reclining photographing position to the position storing portion 43.

The upper/lower position detector 413 is disposed in the upper/lower driving mechanism 313 of the tabletop moving mechanism 31, and detects a position of the second support 122 being driven with respect to the third support 123, to thereby detect a position (upper/lower moving position) of the tabletop 11 moving in the upper/lower direction. Then, the upper/lower position detector 413 outputs the detected upper/lower moving position to the mechanism controlling portion 33.

The upper/lower position detector 413 also detects a position in the upper/lower direction at the photographing position T3 (upper/lower photographing position) of the tabletop 11 when the object P is positioned with respect to the arm 23 at the photographing position T1, and outputs the detected upper/lower photographing position to the position storing portion 43.

The arm position detector 42 is disposed in the arm moving mechanism 32 of the moving mechanism portion 30, and detects a position of the arm 23 moving in the L5 direction and the L6 direction, and outputs the detected position to the mechanism controlling portion 33. The arm position detector 42 also detects the photographing position T1 and the retraction position T2 of the arm 23, and outputs the detected positions to the position storing portion 43.

The position storing portion 43 stores, in a time-series manner, the photographing position T1 of the arm 23 detected by the arm position detector 42 in association with the photographing position T3 of the tabletop 11 defined by the longitudinal photographing position, the raising/reclining photographing position, and the upper/lower photographing position that are respectively detected by the longitudinal position detector 411, the raising/reclining position detector 412, and the upper/lower position detector 413 of the tabletop position detector 41 at the photographing position T1. The position storing portion 43 also stores, in a time-series manner, the retraction position T2 detected by the arm position detector 42.

Hereinafter, with reference to FIG. 1 to FIG. 6, an example operation of the X-ray diagnostic apparatus 100 is described.

Figure 4:
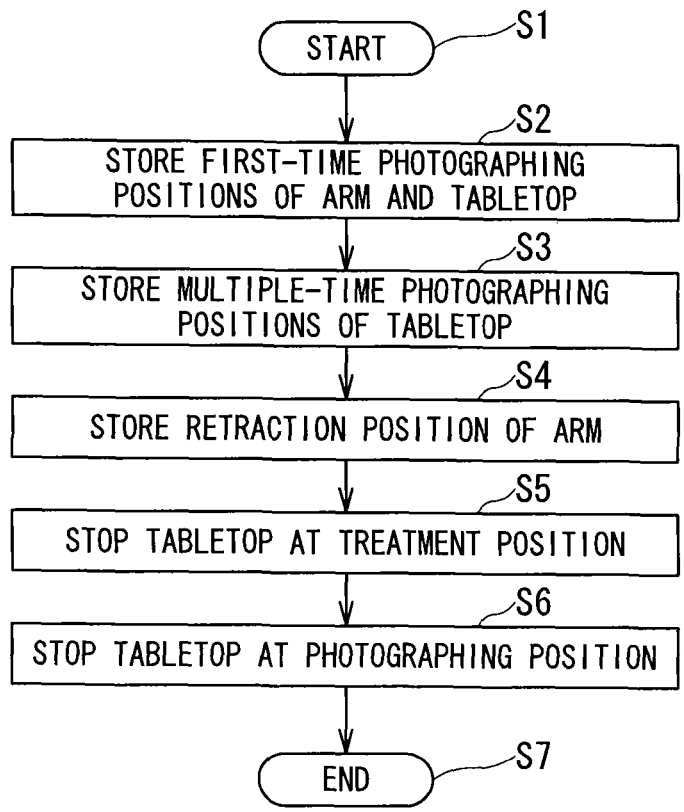
FIG. 4 is a flow chart showing an operation of the X-ray diagnostic apparatus according to the embodiment.

FIG. 4 is a flow chart showing the operation of the X-ray diagnostic apparatus 100. The arm 23 of the radiography unit 20 is stopped at the retraction position T2 at an angle at which the X-ray irradiating portion 21 is located at a lower end of the arm 23 and the X-ray detecting portion 22 is located at an upper end thereof. The object P is placed on the tabletop 11 of the bed portion 10. Then, for the purpose of, for example, performing surgical treatment on the object P, if an input of examination start is made through the operation portion 80, the X-ray diagnostic apparatus 100 starts its operation (Step S1).

The system controlling portion 90 instructs the radiography unit 20, the moving mechanism portion 30, the position detecting portion 40, the high voltage generating portion 50, and the image data generating portion 60 to perform the examination. Then, if an input of moving the arm 23 from the retraction position T2 to the photographing position T1 is made through the operation portion 80, the arm moving mechanism 32 moves the arm 23 in the L5 direction, and stops the arm 23 at the photographing position T1. Subsequently, for the purpose of performing the surgical treatment on the interest part R of the object P, if an input of moving the tabletop 11 to a position at which photographing by the radiography unit 20 is possible is made through the operation portion 80, the tabletop moving mechanism 31 moves the tabletop 11 to align the interest part R of the object P onto the isocenter C at the photographing position T1, and stops the tabletop 11 at the photographing position T3 at which the interest part R can be irradiated with X-rays. The position storing portion 43 stores the photographing positions T1 and T3 at which the arm 23 and the tabletop 11 are respectively stopped first time, the photographing positions T1 and T3 being respectively detected by the arm position detector 42 and the tabletop position detector 41 (Step S2).

Next, if an input of, for example, fluoroscopy start is made through the operation portion 80, the high voltage generating portion 50 supplies, to the X-ray irradiating portion 21, a high voltage for generating X-rays for the fluoroscopy. The X-ray irradiating portion 21 irradiates, with X-rays, the object P placed on the tabletop 11 at the photographing position T3. The X-ray detecting portion 22 detects X-rays transmitted through the object P to generate X-ray projection data. The image data generating portion 60 generates image data from the X-ray projection data generated by the X-ray detecting portion 22. The display portion 70 displays the image data generated by the image data generating portion 60.

During the surgical treatment after the input of examination start, for example, if an input of moving the tabletop 11 to a plurality of the photographing positions T3 is made more than once through the operation portion 80, the tabletop moving mechanism 31 moves the tabletop 11, and the position storing portion 43 stores the photographing positions T3 of the tabletop 11 that are detected more than once by the tabletop position detector 41, in association with the first-time photographing position T1 (Step S3).

Next, for the purpose of performing the surgical treatment while suspending the photographing, if an input of fluoroscopy stop and then an input of moving the arm 23 to the retraction position T2 are made through the operation portion 80, the arm moving mechanism 32 moves the arm 23 in the L6 direction from the photographing position T1, and stops the arm 23 at the retraction position T2. After the stop of the arm 23 at the retraction position T2, the position storing portion 43 stores the retraction position T2 detected by the arm position detector 42 (Step S4).

Subsequently, for the purpose of changing a position of the object P in the raising/reclining direction, if an input of moving the tabletop 11 in the raising/reclining direction and stopping the tabletop 11 at a desired treatment position, is made through the operation portion 80, the mechanism controlling portion 33 controls, in response to the input of moving in the raising/reclining direction, the tabletop moving mechanism 31 on the basis of: the photographing positions T1 and T3 and the retraction position T2 that are stored by the position storing portion 43 during the examination of the object P; and the position of the tabletop 11 outputted by the tabletop position detector 41.

Then, in the case where the arm 23 is stopped at the retraction position T2, the tabletop 11 at the photographing position T3, on which the object P is placed, is moved in the raising/reclining direction and the upper/lower direction such that a position in the upper/lower direction of a region of the object P is maintained, the region corresponding to a position of the isocenter C of the arm 23 at the photographing position T1 that is stored by the position storing portion 43 in association with the photographing position T3 of the tabletop 11. Then, the tabletop 11 is stopped at a treatment position (Step S5).

Note that, in the case where the position storing portion 43 stores a plurality of the photographing positions T1, the tabletop 11 at the photographing position T3 may be moved in the raising/reclining direction and the upper/lower direction such that a position in the upper/lower direction of a region of the object P is maintained, the region corresponding to a position of the isocenter C of the arm 23 at the latest photographing position T1.

Figure 5:
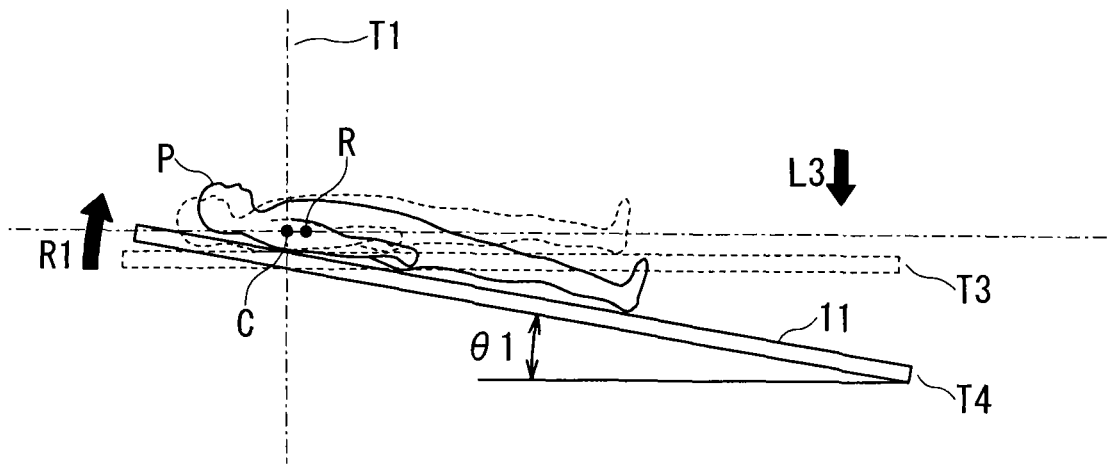
FIG. 5 is a view illustrating an example of a tabletop stopped at a treatment position according to the embodiment.

FIG. 5 is a view illustrating an example of the tabletop 11 stopped at a treatment position. The tabletop 11 in FIG. 5 is moved, for example, by an angle θ1 in the R1 direction from the latest photographing position T3 stored by the position storing portion 43, and is stopped at a treatment position T4 at which the interest part R of the object P is at the same height as that of the isocenter C at the latest photographing position T1.

Here, description is given in detail of control by the mechanism controlling portion 33 for moving the tabletop 11 at the photographing position T3 illustrated in FIG. 5 in the R1 direction and stopping the tabletop 11 at the treatment position T4.

Figure 6:
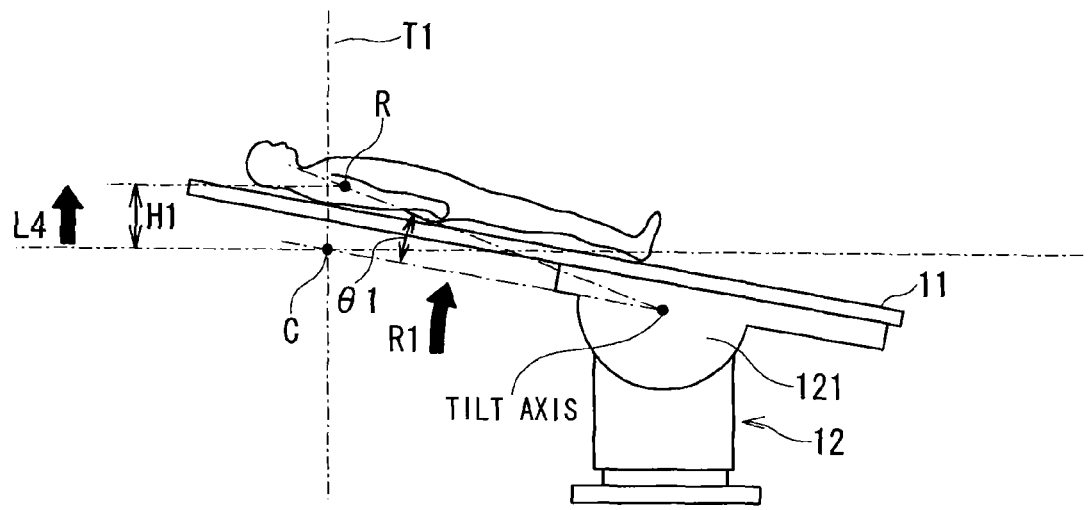
FIG. 6 is a view for describing control for stopping the tabletop at the treatment position according to the embodiment.

During a stand-by state before an input of examination start or after an input of examination end through the operation portion 80, if an input of moving the tabletop 11 by the angle θ1 in the R1 direction is made, the raising/reclining driving mechanism 312 of the tabletop moving mechanism 31 rotationally drives the first support 121 as illustrated in FIG. 6, whereby the tabletop 11 that is disposed at a position away from the isocenter C at the photographing position T1 is rotated along the tilt axis parallel to the lateral direction of the tabletop 11. The raising/reclining driving mechanism 312 moves the tabletop 11 by this rotation in the R1 direction. As a result, the tabletop 11 is stopped at a position at which the interest part R of the object P has moved by a distance H1 in the L4 direction.

Accordingly, the mechanism controlling portion 33 moves the tabletop 11 in the R1 direction and the L3 direction at a given speed, in response to an input of moving the tabletop 11 in the R1 direction. The mechanism controlling portion 33 moves the tabletop 11 in the L3 direction at the same timing as that of moving the tabletop 11 in the R1 direction. The mechanism controlling portion 33 spends a given period of time in moving the tabletop 11 by the distance H1 in the L3 direction, the given period of time being the same as that of moving the tabletop 11 by the angle θ1 in the R1 direction. Then, the mechanism controlling portion 33 stops the tabletop 11 at the treatment position T4.

As described above, because the position storing portion 43 stores the photographing positions T1 and T3 and the retraction position T2, in response to an input of moving the tabletop 11 in the raising/reclining direction after the movement of the arm 23 to the retraction position T2, the tabletop 11 can be moved in the raising/reclining direction in the state where a height of the interest part R of the object P at the photographing position T3 is kept substantially constant. This eliminates the need for an input of moving the tabletop 11 in the upper/lower direction to adjust the height thereof, and hence an amount of work on an operator of the X-ray diagnostic apparatus 100 can be reduced.

Note that, in the case where the number of the same photographing positions T3 that are stored by the position storing portion 43 during the examination of the object P is more than one, the tabletop 11 may be moved to the photographing position T3 at which the tabletop 11 is stopped the largest number of times, and the tabletop 11 at this photographing position T3 may be moved in the raising/reclining direction and the upper/lower direction to be stopped at the treatment position.

In addition, the position storing portion 43 may store examination information inputted through the operation portion 80, a position corresponding to the interest part R of the object P may be determined on the basis of an examination region, an age, a height, and the like contained in the examination information, and the tabletop 11 may be moved in the raising/reclining direction without changing a height of the determined position.

For the purpose of restarting the photographing, if an input of moving the arm 23 to the photographing position T1 is made through the operation portion 80, the mechanism controlling portion 33 controls the tabletop moving mechanism 31 on the basis of the latest photographing position T3 associated with the latest photographing position T1 stored by the position storing portion 43. Then, in response to the input of moving the arm 23 to the photographing position T1, the tabletop 11 at the treatment position T4 is moved in the raising/reclining direction and the upper/lower direction such that a position in the upper/lower direction of the interest part R of the object P is maintained, the object P being positioned with respect to the arm 23 at the latest photographing position T1 stored by the position storing portion 43. Then, the tabletop 11 is stopped at the latest photographing position T3 corresponding to the latest photographing position T1 stored by the position storing portion 43 (Step S6 in FIG. 4).

In this step, in response to the input of moving the arm 23 to the photographing position T1, the mechanism controlling portion 33 moves the tabletop 11 at the treatment position T4 illustrated in FIG. 5, in the R2 direction and the L4 direction at a given speed. The mechanism controlling portion 33 moves the tabletop 11 in the L4 direction at the same timing as that of moving the tabletop 11 in the R2 direction. The mechanism controlling portion 33 spends a given period of time in moving the tabletop 11 by the distance H1 in the L4 direction, the given period of time being the same as that of moving the tabletop 11 by the angle θ1 in the R2 direction. Then, the mechanism controlling portion 33 stops the tabletop 11 at the photographing position T3 illustrated in FIG. 5. The position storing portion 43 stores the photographing position T3 on the basis of a position detected by the tabletop position detector 41.

After the stop of the tabletop 11 at the photographing position T3, the arm moving mechanism 32 moves the arm 23 in the L5 direction from the retraction position T2, and stops the arm 23 at the photographing position T1. After the stop of the arm 23 at the photographing position T1, the position storing portion 43 stores the photographing position T1 on the basis of a position detected by the arm position detector 42.

As described above, in the case where the arm 23 at the retraction position T2 is returned to the photographing position T1 during the examination, the tabletop 11 can be moved to the latest photographing position T3 determined when the object P is positioned with respect to the arm 23 at the photographing position T1.

Next, for example, an input of fluoroscopy start is made through the operation portion 80, the surgical treatment is ended, and an input of fluoroscopy stop is made through the operation portion 80. Subsequently, if an input of moving the arm 23 in the retraction position T2 is made, the arm moving mechanism 32 moves the arm 23 in the L6 direction from the photographing position T1, and stops the arm 23 at the retraction position T2.

Then, if an input of examination end is made through the operation portion 80, the system controlling portion 90 instructs the radiography unit 20, the moving mechanism portion 30, the position detecting portion 40, the high voltage generating portion 50, and the image data generating portion 60 to end the examination, whereby the X-ray diagnostic apparatus 100 stops its operation (Step S7 in FIG. 4).

According to the embodiment described above, because the position storing portion 43 stores the photographing positions T1 and T3 and the retraction position T2, in response to an input of moving the tabletop 11 in the raising/reclining direction after the movement of the arm 23 to the retraction position T2, the tabletop 11 is moved in the raising/reclining direction and the upper/lower direction, whereby the tabletop 11 can be moved in the raising/reclining direction in the state where a height of the interest part R of the object P at the photographing position T3 is kept substantially constant. In addition, in the case where the arm 23 at the retraction position T2 is returned to the photographing position T1 during the examination, the tabletop 11 can be moved to the latest photographing position T3 determined when the object P is positioned with respect to the arm 23 at the latest photographing position T1.

This eliminates the need for an input of moving the tabletop 11 in the upper/lower direction to adjust the height thereof, and hence an amount of work on an operator can be reduced.

Note that the present invention is not limited to the above-mentioned embodiment. For example, in Step S5 in FIG. 4, in response to the input of moving in the raising/reclining direction, the tabletop 11 at the latest photographing position T3 stored by the position storing portion 43 may be moved in the raising/reclining direction, the upper/lower direction, and the longitudinal direction such that a position in the upper/lower direction of the interest part R of the object P and a position in the approaching/separating direction of the arm 23 are maintained, the object P being positioned with respect to the arm 23 at the latest photographing position T1 stored by the position storing portion 43.

Figure 7:
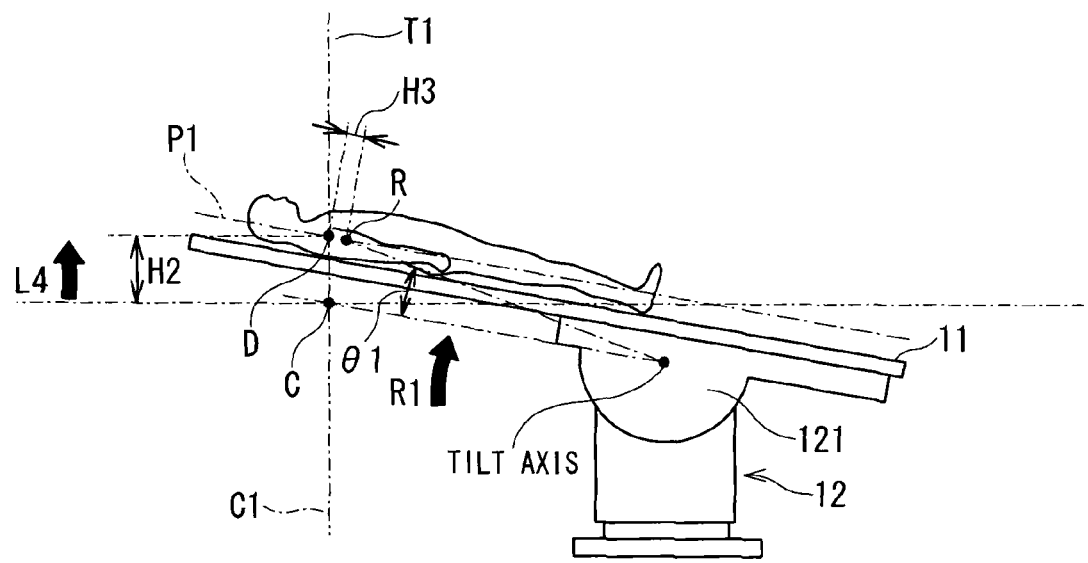
FIG. 7 is a view for describing control for stopping the tabletop at the treatment position according to the embodiment.

In this case, if an input of moving the tabletop 11 by the angle θ1 in the R1 direction is made through the operation portion 80 during a stand-by state, as illustrated in FIG. 7, the tabletop 11 is stopped at a position at which an intersection point D between a straight line P1 and a straight line C1 has moved in the L4 direction from the isocenter C by a distance H2 longer than the distance H1, the straight line P1 passing through the interest part R and being parallel to the longitudinal direction of the tabletop 11 that is stopped at a position after the movement thereof by the angle θ1 in the R1 direction, the straight line C1 passing through the isocenter C and extending in the upper/lower direction. In addition, a distance between the intersection point D and the interest part R on the straight line P1 is a distance H3.

Figure 8:
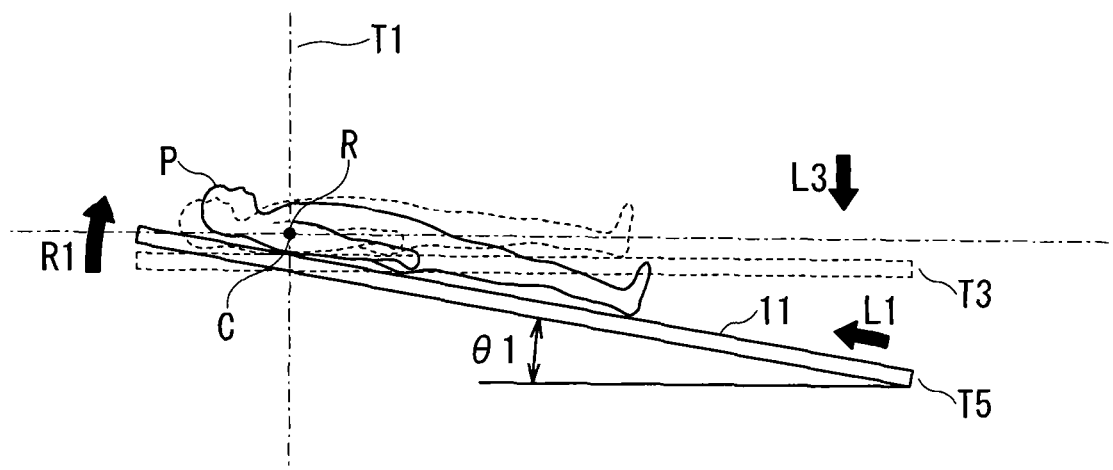
FIG. 8 is a view illustrating another example of the tabletop that is stopped at the treatment position according to the embodiment.

Accordingly, the mechanism controlling portion 33 moves the tabletop 11 in the R1 direction, the L3 direction, and the L1 direction at a given speed, in response to an input of moving the tabletop 11 in the R1 direction. The mechanism controlling portion 33 moves the tabletop 11 in the L3 direction and the L1 direction at the same timing as that of moving the tabletop 11 in the R1 direction. The mechanism controlling portion 33 spends a given period of time in moving the tabletop 11 by the distance H1 in the L3 direction and moving the tabletop 11 by the distance H3 in the L1 direction, the given period of time being the same as that of moving the tabletop 11 by the angle θ1 in the R1 direction. Then, as illustrated in FIG. 8, the mechanism controlling portion 33 stops the tabletop 11 at a treatment position T5 at which the isocenter C at the photographing position T1 coincides with the position in the upper/lower direction of the interest part R and the position in the approaching/separating direction of the arm 23.

As described above, because the position storing portion 43 stores the photographing positions T1 and T3 and the retraction position T2, in response to an input of moving the tabletop 11 in the raising/reclining direction after the movement of the arm 23 to the retraction position T2, the tabletop 11 is moved in the raising/reclining direction, the upper/lower direction, and the longitudinal direction, whereby the tabletop 11 can be moved in the state where a height of the interest part R of the object P on the tabletop 11 at the latest photographing position T3 is kept substantially constant. This eliminates the need for an input of moving the tabletop 11 in the upper/lower direction to adjust the height thereof, and hence an amount of work on an operator can be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
   a tabletop on which an object is placed;
   a tabletop support configured to support the tabletop movably in a longitudinal direction, a raising/reclining direction, and an upper/lower direction of the tabletop;
   an arm configured to hold an X-ray tube and an X-ray detector movably in an approaching/separating direction with respect to the tabletop support, the X-ray tube being configured to irradiate the object placed on the tabletop with X-rays, the X-ray detector being configured to detect X-rays transmitted through the object;
   a position storing unit configured to store a photographing position of the arm and a photographing position of the tabletop in association with each other for each photographing of the object; and
   a mechanism controlling unit configured to move, when the arm is at a retraction position at which irradiation of the object on the tabletop with X-rays is impossible, the tabletop in the raising/reclining direction and the upper/lower direction so as to maintain a position in at least the upper/lower direction of a region of the object corresponding to a photographing position of the arm stored by the position storing unit.

2. The X-ray diagnostic apparatus according to claim 1, wherein
   the mechanism controlling unit is configured to move the tabletop in the raising/reclining direction, the upper/lower direction, and the longitudinal direction so as to maintain the position in the upper/lower direction and a position in the approaching/separating direction of the region of the object.

3. The X-ray diagnostic apparatus according to claim 1, wherein
   the photographing position of the arm that is adopted by the mechanism controlling unit when the arm is at the retraction position is a latest photographing position of the arm stored by the position storing unit.

4. The X-ray diagnostic apparatus according to claim 1, wherein
   the photographing position of the arm that is adopted by the mechanism controlling unit when the arm is at the retraction position is a position at which the arm is stopped the largest number of times, among a plurality of photographing positions of the arm stored by the position storing unit.

5. The X-ray diagnostic apparatus according to claim 1, wherein
   the mechanism controlling unit is configured to move, before moving the arm at the retraction position to a latest photographing position of the arm stored by the position storing unit, the tabletop in advance to a latest photographing position of the tabletop associated with the latest photographing position of the arm stored by the position storing unit.

* * * * *